United States Patent

McMullan et al.

[11] 4,072,424
[45] Feb. 7, 1978

[54] OPTICAL DEVICE FOR MEASURING THE TURBIDITY OF A LIQUID

[76] Inventors: James P. McMullan; Albert Stevens, both of 2630 Seaman Ave., El Monte, Calif. 91733

[21] Appl. No.: 653,739

[22] Filed: Jan. 30, 1976

[51] Int. Cl.² .................................... G01N 21/26
[52] U.S. Cl. .................................. 356/208; 250/573
[58] Field of Search ............... 356/201, 207, 208; 350/63; 250/573, 576, 227

[56] References Cited

U.S. PATENT DOCUMENTS

| | | | |
|---|---|---|---|
| 3,861,198 | 1/1975 | Shea | 356/208 |
| 3,906,241 | 9/1975 | Thompson | 250/227 |
| 3,954,342 | 5/1976 | Boeke | 356/207 |

Primary Examiner—Vincent P. McGraw
Attorney, Agent, or Firm—Georges A. Maxwell

[57] ABSTRACT

A turbidimeter having an elongate fluid conducting body with an access opening at one end and spaced fluid inlet and outlet openings with means to connect the body between sections of a fluid conducting line, a plug-like service unit releasably engaged with and normally closing the body, a light emitter, a conducting light pipe conducting light from the emitter to the end of the body remote from the unit and directing light back towards the unit, a first photo cell carried by the unit and receiving light directed by the light pipe, a second photo cell matched with the first photo cell heat sink means to equalize the temperatures of the cells, power supply and signal transmitting means for the emitter and for the cells, said signal transmitting means including means comparing the signals from the cells.

10 Claims, 10 Drawing Figures

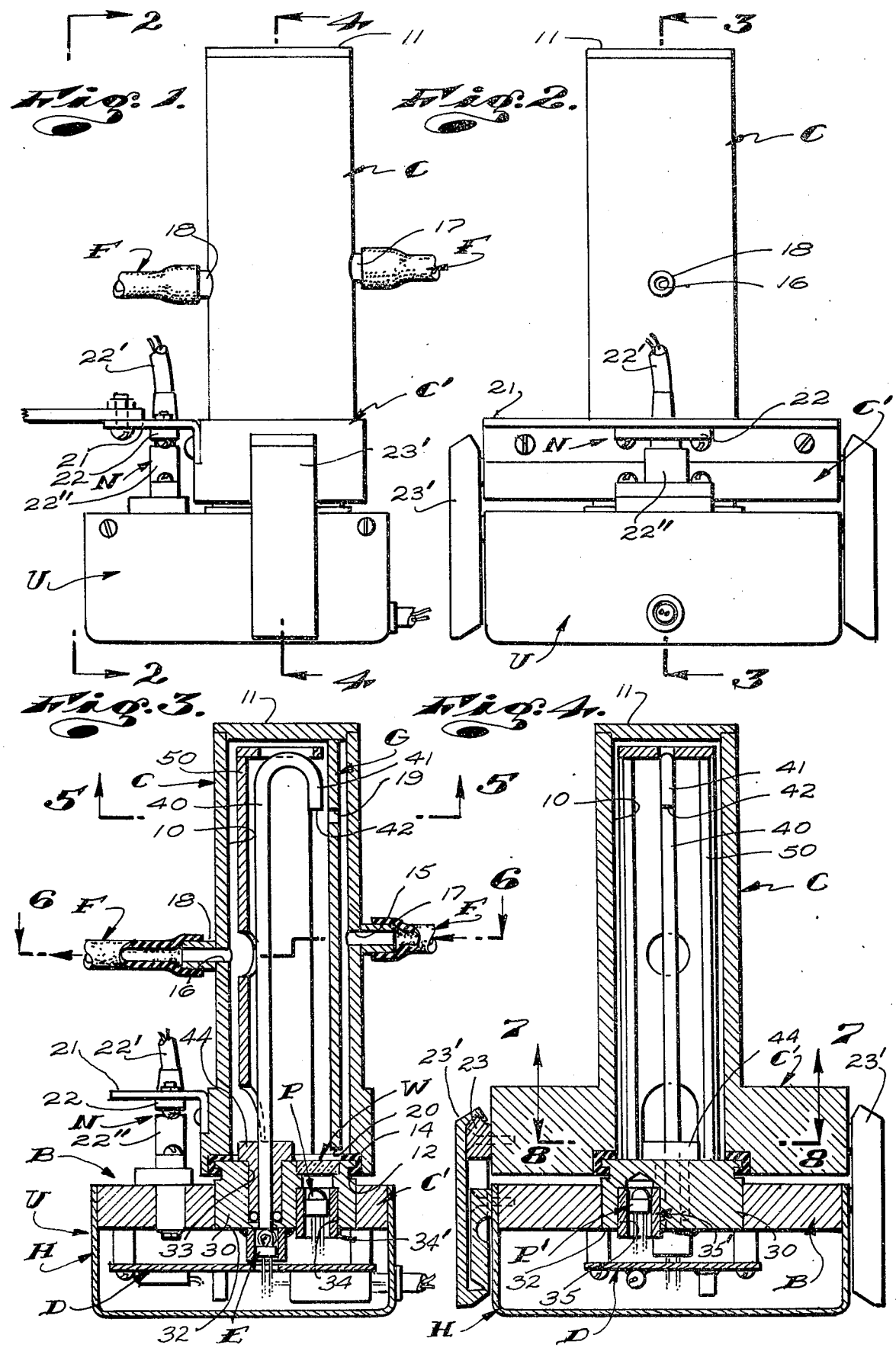

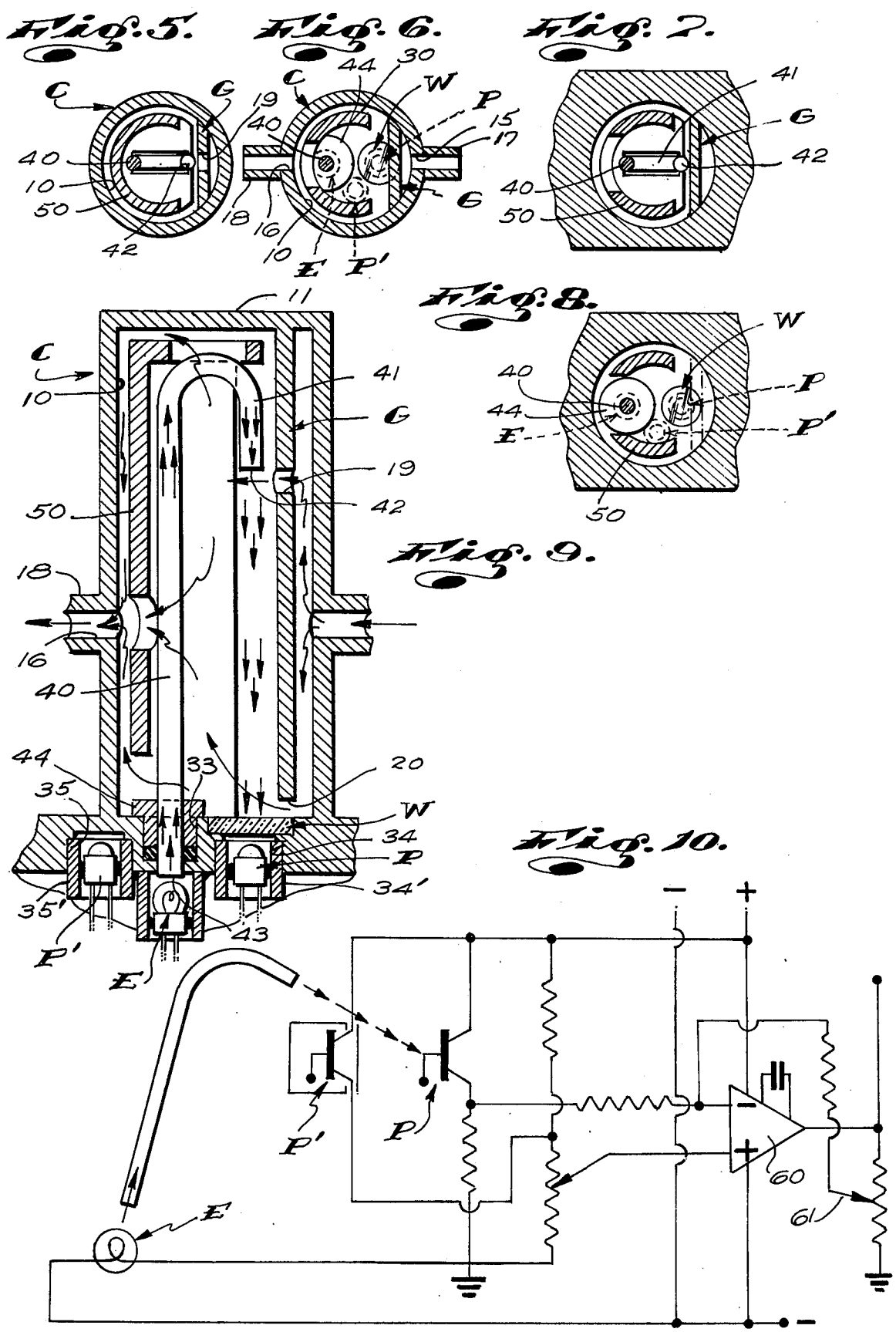

OPTICAL DEVICE FOR MEASURING THE TURBIDITY OF A LIQUID

This invention has to do with an optical device for measuring the turbidity of a fluid, hereafter called a turbidimeter and is more particularly concerned with an improved structure which enables the instrument to be most advantageously and effectively incorporated in a desired fluid handling apparatus or system as a component part thereof.

Turbidimeters (also commonly named "nephelometers") are instruments for comparing the turbidity of liquids by viewing light through them and determining how much light is cut off by them, or otherwise defined as instruments for measuring the cloudiness and the character of suspensions in a fluid by means of diffused, transmitted or reflected light.

Throughout the various arts where fluids are handled, treated and otherwise worked upon, it is frequently desired or necessary to watch and guard against variations or changed in the nature and/or character of the fluids, as might be caused by the undesired admixing of certain dilutants or pollutants, the undesired proportional ratio of commingled fluids and/or as might be caused by oxidation or the subjecting of the fluid to excessive variations in temperature and the like.

In many situations where the nature and character of liquids being worked upon must be controlled and/or protected against pollution and the like, the liquids are transparent or translucent and their light conducting capacity is varied, altered or changed when the nature and/or character of liquids is altered or changed, as by the presence of pollutants. In such situations, it has long been common practice in the art to periodically obtain samples of such fluids and to inspect or examine them by means of a turbidimeter and to thereby maintain those controls which are desired or required.

The above noted procedure of periodically obtaining and examining samples of liquids for independent examination by means of a turbidimeter is slow, oftentimes extremely complicated and does not lend itself to the continuous accurate monitoring of liquids.

In many situations it is necessary or imperative that a liquid be subject to continuous monitoring and/or control and that automatic means be provided that will continuously monitor the turbidity of the liquid. It is desirable that such automatic means be connected with appropriate, related control means in their related fluid handling systems or apparatus.

In the last noted situation, it has become common practice to provide in-line turbidimeters which are such that they can be advantageously engaged in a line or pipe through which the fluid to be monitored is conducted. These in-line turbidimeters are rather simple devices or instruments and characteristically include short, sub-like fluid conducting bodies engageable with and between related pipe sections and have pairs of window openings in diametrically opposite sides to enable the passage of light through the liquids. The window openings are closed and sealed by transparent quartz or glass panes. In each such case, light emitting means, such as an incandescent lamp is positioned at the outside of one window to direct light through that window and the other window and a photo electric cell is positioned at the outside of the other window and is disposed to receive the light emitted from the emitter. The cell is connected with suitable electric circuitry to record the amount of light detected thereby and/or to effect operation of suitable fluid control means in response to changes in the light detected thereby.

While the above, simple, basic form of in-line turbidimeter has proved to be reasonably effective, in some situations, it has proved to be seriously wanting in several respects.

A major shortcoming of the above noted basic form of in-line turbidimeter resides in the fact that it cannot be services or cleaned without removing the entire instrument from engagement in the line or pipe in which it is engaged, which is oftentimes a complicated costly operation and results in considerable down time of the apparatus with which it is related.

It is to be noted and understood that solid matter and the like which is in or carried by the fluids tend to collect on the windows, cutting off the light which is supposed to pass therethrough and which results in a false reading by the instrument. Accordingly, it is often extremely important that the windows be regularly cleaned.

In addition to matter collecting on and about the windows of such instruments, air or gas in and carried by the fluids tend to collect in the form of light reflecting or refracting bubbles on the windows. The formation of such bubbles on the windows is a common and serious cause of malfunction of such instruments. Some instruments have removable windows to facilitate cleaning. Removal of such windows generally requires that the light emitter and cell first be disconnected and removed to afford access to the windows. Such a procedure is frequently more time-consuming and complicated than simply removing the entire instrument from the pipe and cleaning the windows by simply running a cleaning element through the passage.

Another and most serious shortcoming found to exist in the ordinary or basic form of turbidimeter of the general character referred to above resides in the fact that the photo cells are extremely sensitive and responsive to heat and are such that their signal output in response to impinging light is subject to material change in response to temperature changes in or of the cells. As a result of the foregoing, the ordinary turbidimeter of the class and/or character referred to above is only accurate and dependable in those situations where temperatures remain fixed or constant and where the output of the cells is first set and adjusted for operation at the fixed operating temperature of their related system or apparatus.

In those situations where variations in temperature occur and such changes alter the temperature of the photo cells or turbidimeters, the turbidimeters are not accurate or dependable and require constant adjustment to compensate for temperature variations.

An object and feature of our invention is to provide a new and improved in-line turbidimeter which can be easily, conveniently and quickly cleaned as circumstances require.

It is another object and feature of the invention to provide an instrument of the character referred to wherein the direction and rate of flow of the fluid is slowed and changed whereby foreign matter or the like in the fluid is caused to disburse and/or meander therein and in such a manner that its presence in the liquid is readily detectable by the instrument.

Yet another object and feature of the instant invention is to provide an improved turbidimeter of the general character referred to wherein light from the emitter is conducted through the structure and the liquid by means of a light pipe and is directed toward a related photo cell and through the liquid from a location which is remote from the emitter.

It is an object and feature of our invention to provide a turbidimeter of the general character referred to which includes a pair of like photo cells, one adapted to be impinged upon by light from the emitter and the other being blind or shielded from all impinging light. Both cells are in common heat conducting relationship with related structure whereby they are both at the same temperature and are connected with a signal comparing means in a related signal transmitting circuit, whereby variations in the output signal of said one cell resulting from changes in temperature are continually zeroed out or compensated for.

The foregoing and other objects and features of the present invention will be recognized and fully understood from the following detailed description of a typical preferred form and carrying out of the invention throughout which description reference is made to the accompanying drawings, in which:

FIG. 1 is an elevational view showing one side of our turbidimeter;

FIG. 2 is an elevational view of another side and taken as indicated by line 2—2 on FIG. 1;

FIG. 3 is a sectional view taken as indicated by line 3—3 on FIG. 2;

FIG. 4 is a sectional view taken as indicated by line 4—4 on FIG. 1;

FIG. 5 is a sectional view taken as indicated by line 5—5 on FIG. 3;

FIG. 6 is a sectional view taken as indicated by line 6—6 on FIG. 3;

FIG. 7 is a sectional view taken as indicated by line 7—7 on FIG. 4;

FIG. 8 is a sectional view taken as indicated by line 8—8 on FIG. 4;

FIG. 9 is an enlarged sectional and diagrammatic fiew of a portion of the structure shown on FIG. 3 of the drawings; and FIG. 10 is a circuit diagram.

Referring to the drawings, the turbidimeter that we provide includes two basic, unitary components, one being a fluid conducting chest C and the other a service unit U.

The chest C is an elongate, cylindrical, tubular element which, for the purpose of this disclosure, is shown arranged with its central axis extending vertically. The chest C is characterized by a central vertically opening chamber 10 with a downwardly opening lower end and an upper end closed by a top wall 11.

The lower end portion of the chest C is provided with an enlarged mounting block C' with flat, horizontal top and bottom surfaces and vertical sides.

The chamber 10 enters at the bottom surface of the block C'. The block is provided with a radially inwardly and downwardly opening annular channel or recess 12 about the lower end of the chamber and a sealing ring 14 is seated in said recess.

For the purpose of this disclosure, the chest C can and will be said to have upstream and downstream sides.

The chest C next includes inlet and outlet ports 15 and 16 at its upstream and downstream side and located substantially midway between the upper and lower ends of the chamber. The chest is provided with connecting means communicating with the ports and adapted to connect with sections of a flow line F with which the structure is related. The connecting means is shown as including simple elongate nipples 17 and 18 projecting radially outwardly from the chest. The flow line F is shown as comprising sections of rubber hose with ends engaged on and about said nipples.

In addition to the foregoing, the chest C is provided with baffle means G within the chamber 10 to control and direct the flow of fluid entering the chamber through the port 15, vertically upwardly and downwardly and thence horizontally in a downstream direction, as will be particularly described in the following:

The baffle means G is shown as including a flat vertical partition arranged in the chamber 10 at the upstream side or portion thereof, and in spaced overlying relationship with the port 15. The partition is shown as having a port 19 in its upper portion and a straight horizontal lower edge 20 in predetermined spaced relationship above the lower open end of the chamber, adjacent the recess 12.

The chest C in addition to the foregoing structure includes and/or carries elements and parts of related means. For example, the chest is provided with and carries a mounting bracket 21 to facilitate mounting the chest in a fixed position in and relative to related fluid handling apparatus; a member 22 of an electrical connecting means N provided to establish necessary electrical connection between the structure and related power supply means and the like; and elements or parts 23 of releasable latch means M provided to normally releasably secure the chest C and unit U in assembled relationship, as will hereinafter be described.

The member 22 of the means N referred to above is shown as including a male plug element carried by the bracket 21 to depend therefrom and to oppose the top of the unit U and as having an electrical cable or service loom 22' extending upwardly therefrom. The parts 23 of the means M are shown as simple cleat like parts fixed to opposite sides of the block C' of the chest C.

The chest structure C set forth above can be established of any desired suitable material and can be established in whole or in part by fabricating and/or molding processes and techniques, as desired or as circumstances require. The single principal requirement in establishing the chest C is that it be a non-light conducting or opaque structure, which requirement can best be afforded or imparted into the structure by the utilization of opaque materials.

The service unit U that we provide includes a central, vertically extending, central cylindrical plug 30 with flat horizontal upper and lower end surfaces 31 and 32. The upper end portion of the plug 30 is normally engaged in the annular recess 12 in the lower end of the chest C and in tight sealing engagement with the sealing ring 14 in said recess. The plug 30 normally closes and seals the lower end of the chamber 10.

The lower portion of the plug 30 depends from the lower end of the chest and is connected with, carries or is integrally joined with a flat horizontal rectangular body B, which body projects radially from the plug to normally occur in spaced relationship below the block C' of the chest C. The plug and body, as indicated above, can be separate parts assembled and fixed together in some suitable manner or can be formed integrally, as desired, or as circumstances require.

The plug 30 is normally in predetermined rotative position relative to the chamber 10 and has upstream and downstream sides. The plug 30 is characterized by a pair of vertical through openings 33 and 34 at its upstream and downstream sides, within the radial limits of the chamber 10 and by a downwardly opening socket 35 which is preferably arranged adjacent to and is circumferentially offset from the opening 33.

The opening 34 is provided with an annular seat in its upper end portion and in which a glass or quartz window W is sealingly engaged and fixed. The window W has a top surface which is substantially flush with the top surface 31 of the plug 30.

In practice, and as shown, the top surface of the window is on a plane spaced a limited distance below and immediately downstream from the lower edge 20 of the partition G in the chamber C, whereby a portion of the fluid flowing into and through the chamber 10 is directed across the top surface of the window and in such a manner as to wash and keep the window clean and free of foreign matter and the accumulation of gas bubbles.

The above washing effect is a highly important feature of our invention and should not be overlooked or discounted.

The unit U next includes an elongate vertical light pipe 40 with a recurvant upper end portion 41 terminating at and/or defining a downwardly disposed light emitting end surface 42 which occurs in vertical spaced and axial alignment relationship with opening 34 and the window W and which occurs on a horizontal plane at and immediately downstream of the port 19 in the partition G of the chest C whereby a portion of the fluid flowing into and through the chamber 10 is directed across the light emitting end surface 42 of the light pipe to wash and maintain that surface of the pipe free of foreign matter and/or gas bubbles.

The lower end portion of the light pipe 40 is engaged in the upper portion of the opening 33 of the plug 30 in fluid tight sealed engagement therewith and with its lower light receiving end 43 disposed downwardly in a free and unobstructed manner toward the lower interior portion of the opening 33. In the case illustrated, the lower end portion of the light pipe 40 is provided with a plug-like base 44 which provides desired support for the pipe and which is engaged in the opening 33, as clearly illustrated in the drawings. Further, a suitable sealing means can be and is shown provided between the plug and the base.

The unit U that we provide next includes a light emitter E carried by the plug 30 adjacent the lower end 43 of the light pipe 40, a first photo cell P in the lower portion of the opening 34 below with its base disposed toward the window W and a second photo cell P' in the downwardly opening socket 35 in the plug, adjacent the opening 34.

In practice, it has been found desirable to provide heat sink means to better equalize and/or stabilize the temperatures of the photo cells. To this end, the sockets 34 and 35 in which the cells are fixed are provided tubular alluminum heat sink inserts 34' and 35' set in the plug portion of the base structure, substantially as shown in the drawings.

The emitter E can be a light emitting diode or a simple incandescent lamp, as desired, or as circumstances require. The photo cells P and P' are alike and are matched photo-electric cells. In practice, the cells P and P' can be any suitable electric signal modifying and transmitting photo sensitive devices.

The emitter E is in substantial direct light conducting relationship with the lower end 43 of the light pipe and in practice, is preferably painted, shielded, or installed to block the emission or random light from those sides and/or surfaces of the emitter which are not directed toward the light pipe.

In accordance with the broader aspects of our invention, the light or matched photo cells P and P' are arranged in the structure so that the cell P is exposed only to that light which issues from the emitter E through the pipe 40 and chamber 10 and thence through the window W. The cell P' is blocked from all light and is therefore black or "blind". The two cells P and P' are so related to the adjacent structure and/or their environment so that they are maintained and essentially or substantially the same temperature at all times during the operation of the construction.

To the above end, the cells P and P' are arranged in the lower portions of their related opening socket in the plug 30 and are secured therein by a suitable heat conducting, opaque cement or potting compound deposited in the lower open ends of said openings, in non-interfering relationship with the light receiving bases or surfaces of the cells.

With this structure and relationship of parts, the cell P' is blind or sealed from light and is in heat conducting relationship with the mass of the plug and the cell P is in heat conducting relationship with the mass of the plug and is only subjected to light from the emitter conducted through the pipe 40 and the fluid in the chamber 10 and which passes through the window W. The plug 30 is in the nature of a heat sink and is such that it changes temperature uniformly in response to changes in temperature of the fluid being handled and/or other parts of the construction related to it. As a result of the above, while the temperature of the cells P and P' might rise and fall, such changes in temperatures occur uniformly in response to changes in temperature of the mass of the plug 30 in and/or with which the cells are arranged and related.

It is to be understood and is believed apparent that in practice the cells P and P' can be related to the plug 30 and the window W and/or with other parts of the construction in a number of different ways to attain the above noted light and/or heat control which is afforded by the particular structure illustrated and described above.

In practice, the light pipe 40 is established of a length of glass fiber rod stock suitably formed, as illustrated. The light pipe 40 is a thin and flexible member of limited strength and stability and is such that it should be afforded appropriate support and shielding to prevent its breakage, distortion and/or misalignment in the structure when in normal use.

In light of the above, the unit U is provided with an elongate vertical light pipe supporting and shielding shell or cage 50 fixed to and projecting upwardly from the plug 30 and freely into the chamber 10 to occur in spaced shielding relationship about the major portion or extent of the light pipe 40 and the upper recurvant portion 41 of the light pipe, substantially as shown in the drawings.

In the form of the invention illustrated, the cage 50 is an elongate vertical semi-tubular part with an open side disposed toward the upstream side of the chamber and with a semi-cylindrical wall extending about the downstream side of the chamber, in spaced relationship with the bore and the vertical, downstream, portion of the pipe. The lower end of the cage is fixed to the plug 30 and its upper end is closed by a top wall provided with a slot or hole in which the portion 41 of the light pipe 40 is engaged. Additionally, the cage is provided with suitable openings and/or ports to permit and/or afford for the free flow of liquid through and about the cage and therefor, in, throughout and from the chamber 10.

In practice, the cage 50 can take many forms without departing from the spirit of our invention. For example, it will be readily apparent that the cage could be effectively established of wire stock and would thereby be imparted with a more conventional cage-like appearance.

The body B of the unit U which occurs below the block C' of the chest C is provided with and/or pivotally carries manually engageable and operable latch members 23' of the means M, which occur at opposite sides of the body and are operable to releasably engage the cleat-like members 23 of the means M occurring on or carried by the block C'. The means M noted above and shown in the drawings, normally releasably holds the body and block in assembled relationship and serves to normally urge the upper portion of the plug 30 in tight sealing engagement with the seal 14 in the recess 12 of the chest C.

The chassis or circuit board D of the unit U is a typical flat, plate-like circuit board which, in the preferred carrying out of the invention is mounted in spaced parallel relationship with and below the body B by means of support posts and screw fasteners, in accordance with common practices and as shown in the drawings.

The housing H is a simple upwardly opening formed metal or plastic cup or box-like part with side walls engaged about the exterior of the body and releasably secured thereby as by means of suitable screw fastening screw fasteners.

The unit U next and finally includes a vertical opening in the body occurring in vertical alignment with the connecting part or male plug member 22 of the means N and a connecting part or female socket member 22" engaged through the noted opening in mounted relationship with the body and projecting upwardly therefrom to cooperatively receive the plug 22 of the means N, when the chest C and unit U are in their normal assembled, operating relationship with each other.

In practice, except for the electrical components, the various elements and/or parts of the unit U, like the chest C, can be established of any suitable material or materials and can be established by any suitable manufacturing processes and/or techniques. It is, however, important and necessary that the plug portion of the unit, with which the emitter E and the cells P and P' are related, be opaque and such that light from the emitter E does not escape from the plug randomly and so that the cells P and P' are not subjected to the effects of random light which might otherwise travel or move through the plug and impinge upon them. With the structure thus far described, it will be noted that the chest C is engaged in and made a part of the fluid handling apparatus or system with which our construction is related and that the service unit U is a separate unit releasably related with the chest and which can be easily, quickly and effectively disengaged from the chest, as for servicing, by simply releasing the latch means M and pulling the unit U downwardly, away from and out of engagement with and/or in the chest. Re-engagement or assembly of the construction is quickly and effectively established, with equal ease, by simply urging the unit U up into engagement in and/or with the chest and re-engaging the latch means M.

The detector is essentially a light differential amplifier with the two cells P and P' acting as input voltage. The cell P receives light from the lamp or emitter E via the light pipe and chamber 10. P' is blind or sees no light. The difference of the signal between P and P' is amplified. If light striking P is reduced as by blood in chamber 10, current from P is reduced. The amplifier means amplifies and inverts this current or signal for use by the kidney machine.

The circuit that we provide and which is related with the emitter E and cells P and P' can vary widely and, as shown in FIG. 10 of the drawings, includes a suitable power source S supplying operating current to the emitter E and a common input voltage to the cells P and P'. The base or principal output voltages from the cells P and P', (though variable in response to temperature variations or changes) are the same. The output voltage of the blind cell P', while variable with the output voltage of the cell P, in response to temperature changes in the structure, is non-variable with respect to light, since it is blind or dark at all times. The output signal of the light responsive cell P, while variable in response to temperature changes, with and to the same extent that the output of the cell P' is variable, is further variable in response to that light from the emitter and light pipe which passes through the fluid in the chamber 10 and impinges upon it. Accordingly, the output of the cell P' is a reference signal with which the signal from the cell P can be and is compared. The difference between the signals from the cells P and P' is that signal or portion of the signal from cell P which corresponds to the amount of light impinging upon that cell. The signal changes effected by heat change are effectively cancelled out.

To effect the above noted signal comparison, the circuit can and as shown, includes a signal comparitor 60 receiving the two signals from the cells P and P' and emitting the differential or resolved signal. The differential signal from the comparitor can be conducted to a potentiometer 61 provided to monitor the construction during its operation and/or can be conducted to suitable electrically operated or controlled flow control devices and/or means of a related apparatus (not shown) for the purpose of effecting direct, continuous and automatic control of the apparatus, as desired, or as circumstances require.

In addition to the few basic elements and components noted above, the circuit can, as noted in FIG. 10 of the drawings, be provided with or include suitable resistors and the like to appropriately balance the various voltages and/or signals and, if desired, to effect adjusting and/or zeroing out the construction or its output signal, in accordance with common practices.

Those elemtns and/or parts of the circuit which are not and need not be directly related to the plug, but which are preferably related directly with the unit U, are carried by the chassis D.

The operating voltage or current directed to and the signal or signals generated in or by and conducted from the unit U are suitably conducted to the member 22" of means N, through the member 22 of that means and thence through the cable or loom 22' which extends from the construction to related support means and the like (not shown).

Summarizing our invention, the most important features are: first, that structure provided whereby the service unit U is in the nature of a plug unit engageable in and with the chest C from one end thereof and which affords for easy convenient and quick servicing of the construction; second, the light pipe and its relationship with the emitter, chamber, window and light responsive photo cell whereby light which is emitted at and sensed at one end of the chamber is effectively projected toward that one end of the chamber from the other or opposite end of the chamber; third, the provision of structural means whereby fluid flowing into and through the chamber is directed across those surfaces within the chamber from which light is emitted and through which light within the chamber must escape, whereby those surfaces are maintained clean of foreign matter and the accumulation of gas bubbles and the like; and, fourth, the provision of a novel circuit utilizing two like photo cells in a common heat environment and where one of said cells is maintained dark or blind, whereby the signal output of the circuit corresponds directly with the amount of light which impinges upon the other of said cells and whereby effects of heat changes upon the cells is compensated for or balanced out.

Having described only typical forms and applications of our invention, we do not wish to be limited to the specific details herein set forth, but wish to reserve for ourselves any modifications and/or variations which may appear to those skilled in the art and which fall within the scope of the following claims:

Having described our invention, we claim:

1. A turbidimeter comprising a chest with an elongate fluid conducting chamber having upstream and downstream sides, inlet and outlet ports communicating with the upstream and downstream sides of the chamber between the ends thereof, flow directing means in the chamber in the upstream side portion thereof directing fluid flowing into the chamber through the inlet port longitudinally outwardly toward the opposite ends and thence toward the downstream side of the chamber, a light emitter at one end of the chest outside the chamber, an elongate light conducting light pipe with an inlet end exposed to the emitter, extending longitudinally freely through the chamber and having a recurvate free end portion with an outlet end in the chamber at the other end portion of the chest and disposed toward said one end of the chest and across which fluid directed toward said other end and thence downstream in the chamber by said flow directing means is directed, a light responsive photo cell at said one end of the chest outside the chamber in alignment with the outlet end of the light pipe, a light conducting window between the cell and chamber with a surface within the chamber and across which fluid directed toward said one end and thence downstream in the chamber by the flow directing means is directed.

2. The turbidimeter set forth in claim 1 wherein said flow directing means includes a longitudinal baffle in the chamber between the inlet port at the upstream side thereof and the axis of the light responsive cell and outlet end of the pipe and openings within the chamber defined by the baffle adjacent to and upstream from the outlet end of the light pipe and the window.

3. The turbidimeter set forth in claim 2 wherein the emitter, light pipe, cell and window are carried by and in a plug removably engaged in said one end of the chest and normally closing the adjacent end of the chamber.

4. The turbidimeter set forth in claim 1 wherein the emitter, light pipe, cell and window are carried by and in a plug removably engaged in said one end of the chest and normally closing the adjacent end of the chamber.

5. The turbidimeter set forth in claim 1 which further includes a blind photo cell obscured from light and in similar temperature environment with the light responsive cell and a signal comparing circuit receiving signals from both cells and transmitting a signal which is equal to the differential between the signals from the cells and proportional to the magnitude of light impinging upon the light responsive cell.

6. The turbidimeter set forth in claim 5 wherein said flow directing means includes a longitudinal baffle in the chamber between the inlet port at the upstream side thereof and the axis of the light responsive cell and outlet end of the pipe and openings within the chamber defined by the baffle adjacent to and upstream from the outlet end of the light pipe and the window.

7. The turbidimeter set forth in claim 6 wherein the emitter, light pipe, cell and window are carried by and in a plug removably engaged in said one end of the chest and normally closing the adjacent end of the chamber.

8. The turbidimeter set forth in claim 5 wherein the emitter, light pipe, cell and window are carried by and in a plug removably engaged in said one end of the chest and normally closing the adjacent end of the chamber.

9. The turbidimeter set forth in claim 1 wherein the emitter, light pipe, cell and window are carried by and in a plug removably engaged in said one end of the chest and normally closing the adjacent end of the chamber, said structure further including a support cage carried by the plug, extending freely into the chamber and engaging and supporting the light pipe and releasable latch means on and between the chest and plug releasably maintaining the plug engaged with the chest.

10. The turbidimeter set forth in claim 5 wherein the emitter, light pipe, cells and window are carried by and in a plug removably engaged in said one end of the chest and normally closing the adjacent end of the chamber, said structure further including a support cage carried by the plug, extending freely into the chamber and engaging and supporting the light pipe and releasable latch means on and between the chest and plug releasably maintaining the plug engaged with the chest.

* * * * *